United States Patent [19]
Wang

[11] Patent Number: 5,697,974
[45] Date of Patent: Dec. 16, 1997

[54] INFLATABLE PROSTHESIS INSERTABLE IN ADJUSTABLE BRASSIERE

[76] Inventor: Sui-Mu Wang, C/O Hung Hsing Patent Service Center, P.O. Box 55-1670, Taipei, Taiwan

[21] Appl. No.: 698,542

[22] Filed: Aug. 15, 1996

[51] Int. Cl.$^6$ .................................................. A61F 2/52
[52] U.S. Cl. .................................................. 623/7
[58] Field of Search .................................................. 623/7

[56] References Cited

U.S. PATENT DOCUMENTS

| | | | |
|---|---|---|---|
| 2,698,436 | 4/1955 | Bernhardt | 623/7 |
| 2,764,759 | 10/1956 | Gazelle | |
| 2,883,987 | 4/1959 | White | |
| 3,266,495 | 8/1966 | Sachs | |
| 4,024,876 | 5/1977 | Penrock | |
| 4,178,643 | 12/1979 | Cox, Jr. | 623/7 |
| 4,671,255 | 6/1987 | Dubrul et al. | 623/7 |
| 5,037,436 | 8/1991 | Heaston | 623/7 |

*Primary Examiner*—John G. Weiss
*Assistant Examiner*—John M. Black

[57] ABSTRACT

A pair of inflatable prosthesis sacs are insertable in two cup portions of an adjustable brassiere each sac including an elastic foam core formed in between an outer layer and an inner layer made of elastic materials, an inflating device directly connectable with a prosthesis check valve formed on the sac for inflating the sac, and a deflating device formed on the sac for deflating the sac, thereby eliminating an air tube connected between an air pump and a brassiere cup in order for making a compact brassiere for its comfortable wearing.

5 Claims, 5 Drawing Sheets

INFLATABLE PROSTHESIS INSERTABLE IN ADJUSTABLE BRASSIERE

BACKGROUND OF THE INVENTION

U.S. Pat. No. 2,764,759 to R. J. Gazelle disclosed a brassiere construction having a pair of hollow expansion elements or balloons inflated by a bulb through a tube connected between the balloons and the bulb. The tube connected between the bulb and the balloons may cause tangling or obstruction to the wearer's body.

U.S. Pat. No. 2,883,987 to P. White disclosed an inflatable attachment for brassiere having a pumping sack 28 communicated with a hollow pocket 24 by tube 26 which is attached to a foundation piece 20 of the brassiere with the foundation piece 20 surrounding a wearer's chest portion. However, the foundation piece 20 as fastened on the wearer's body may influence her comfortableness, such as causing poor skin breathing or hot feeling as shielded by the foundation piece.

The conventional inflatable hollow brassiere, after being inflated, will be pneumatically expanded to lose its elasticity and will influence the wearing Comfortableness and the esthetic feeling of the brassiere.

The present inventor has found the drawbacks of the conventional inflatable brassiere and invented the present compact soft prosthesis sacs insertable in the brassiere for a comfortable wearing.

SUMMARY OF THE INVENTION

The object of the present invention is to provide a pair of inflatable prosthesis sacs insertable in two cup portions of an adjustable brassiere each sac including an elastic foam core formed in between an outer layer and an inner layer made of elastic materials, an inflating device directly connectable with a prosthesis check valve formed on the sac for inflating the sac, and a deflating device formed on the sac for deflating the sac, thereby eliminating the air tube connected between an air pump and a brassiere cup in order for making a compact brassiere for its comfortable wearing.

DETAILED DESCRIPTION

Figure 1:
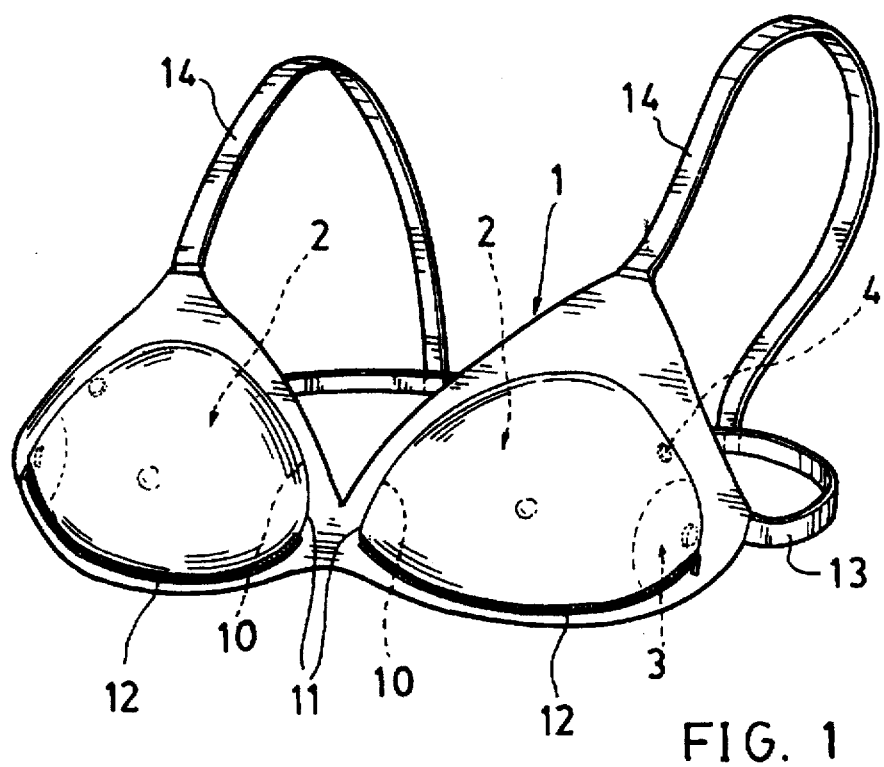
FIG. 1 is a perspective view of the present invention.
Figure 2:
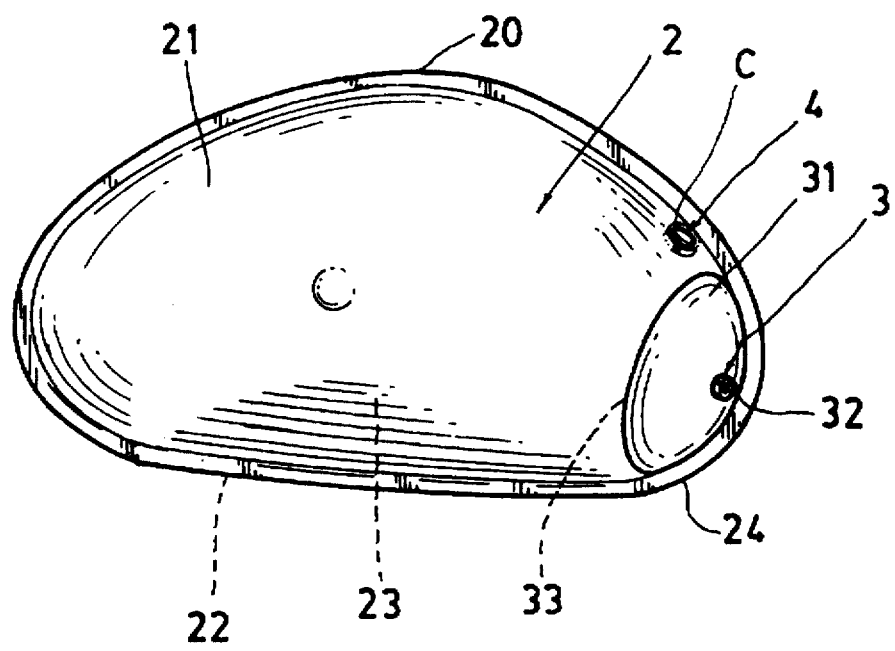
FIG. 2 is a perspective view of the prosthesis sac of the present invention.
Figure 3:
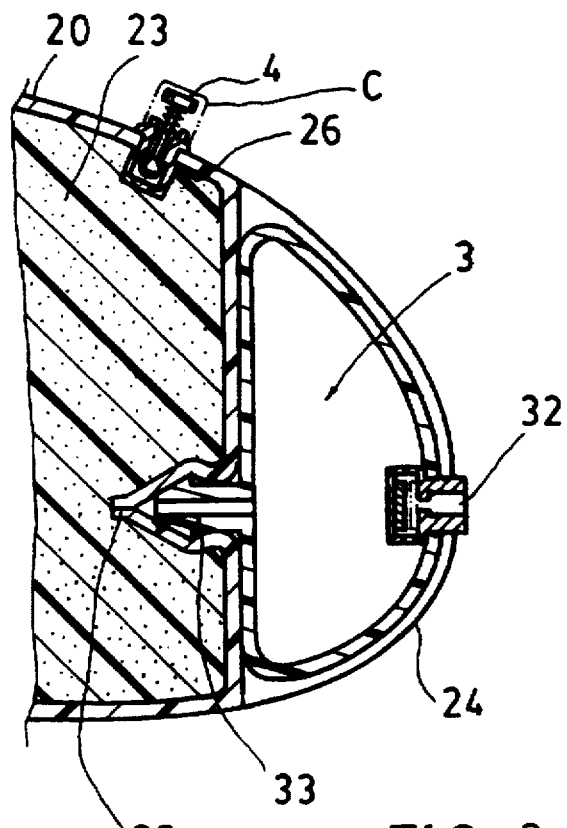
FIG. 3 is a partial sectional drawing of the prosthesis sac of the present invention.
Figure 4:
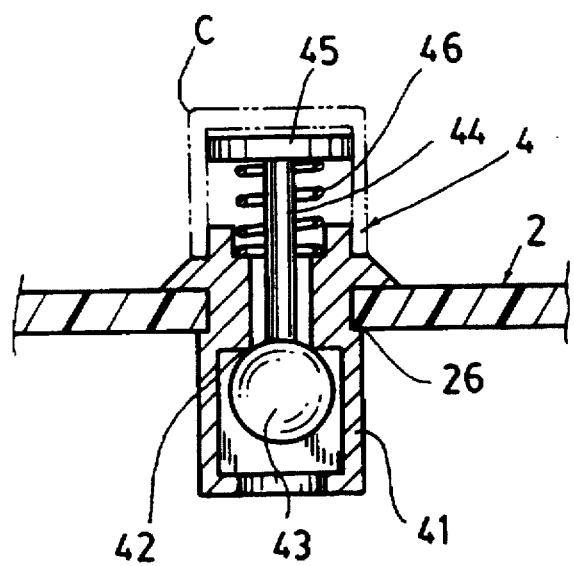
FIG. 4 is an illustration showing the deflating means of the present invention.

As shown in FIGS. 1–6, a preferred embodiment of the present invention comprises: an inflatable prosthesis sac 2 inserted in a cup portion 11 of a brassiere 1, an inflating means 3 connectable with the prosthesis sac 2, and a deflating means 4 formed on the prosthesis sac 2. The brassiere 1 may be an adjustable brassiere having a pair of cup portions 11 each cup portion 11 formed with a pocket 10 therein for receiving each prosthesis sac 2 in the pocket 10 of the cup portion 11, a fastener 12 which may be a zipper fastener or other fasteners for fastening or closing an opening of the pocket 10 for replacing a prosthesis sac as stored in the pocket portion 10, a pair of breast straps 13 laterally connected to the two cup portions 11 to be fastened on a wearer's chest portion, and a pair of shoulder straps 14 connected to the two cup portions 11 for wearing the straps 14 on a girl's shoulders.

Each prosthesis sac 2 generally oval or semispherical shaped includes: an outer layer 21 which may be made of polyurethane leather or other elastic materials; an inner layer 22 also made of polyurethane leather or other elastic materials; a peripheral edge portion 20 circumferentially formed on an edge portion of each outer layer 21 and inner layer 22 by binding or welding each edge portion of the outer layer 21 and the inner layer 22; a sac interior 20a defined between the outer layer 21, the inner layer 22 and the peripheral edge portion 20; a foam core member 23 formed in the sac interior 20a and made of polyurethane foam or other elastomer foams having elasticity thereof; a base extension 24 generally arcuate or triangular shaped and protruding sidewardly from a side portion of the peripheral edge portion 20 for securing the inflating means 3 on the base extension 24; a prosthesis check valve 25 formed on the outer layer 21 or other suitable locations on the sac 2 for coupling the inflating means 3 for inflating the sac 2, and a venting hole 26 formed in the outer layer 21 for inserting the deflating means 4 in the venting hole 26 for deflating the sac 2. A cap C may be provided to cover the deflating means 4 for preventing unexpected depression of the deflating means 4.

The inflating means 3 includes an inflating bulb 31 generally arcuate or triangular shaped to be held on the base extension 24 formed on a side portion of the prosthesis sac 2 to geometrically or circumferentially conform with the contour of the sac 2 and to form an oval shape including the sac 2 and the bulb 31, a suction inlet valve 32 formed on an outer end portion of the bulb 31 for sucking air into the bulb 31, and an adapter 33 formed on an inner portion of the bulb 31 to be connected with the prosthesis check valve 25 in the sac 2 for filling air into the sac 2 through the adapter 33.

The bulb 31 may be made of rubber or other elastic materials, not limited in the present invention.

The deflating means 4 includes: a deflating valve body 41 generally cylindrical shaped and inserted in the venting hole 26 in the sac 2, a valve opening 42 formed in the deflating valve body 41 for venting air outwardly when actuating or opening the deflating means 4, a sealing plug or ball 43 connected with a valve stem 44 protruding outwardly beyond the valve opening 42 with a push button 45 formed on an outermost end of the valve stem 44 and provided for depressing the valve stem 44 and the sealing plug 43 for opening the valve opening 42 for deflating the sac 2, and a restoring spring 46 disposed around the valve stem 44 normally urging the push button 45 outwardly to raise the sealing plug 43 for normally sealing the valve opening 42 and to be ready for depression of the push button 45 for opening the valve opening 42 when actuating the deflating means 4.

Figure 5:
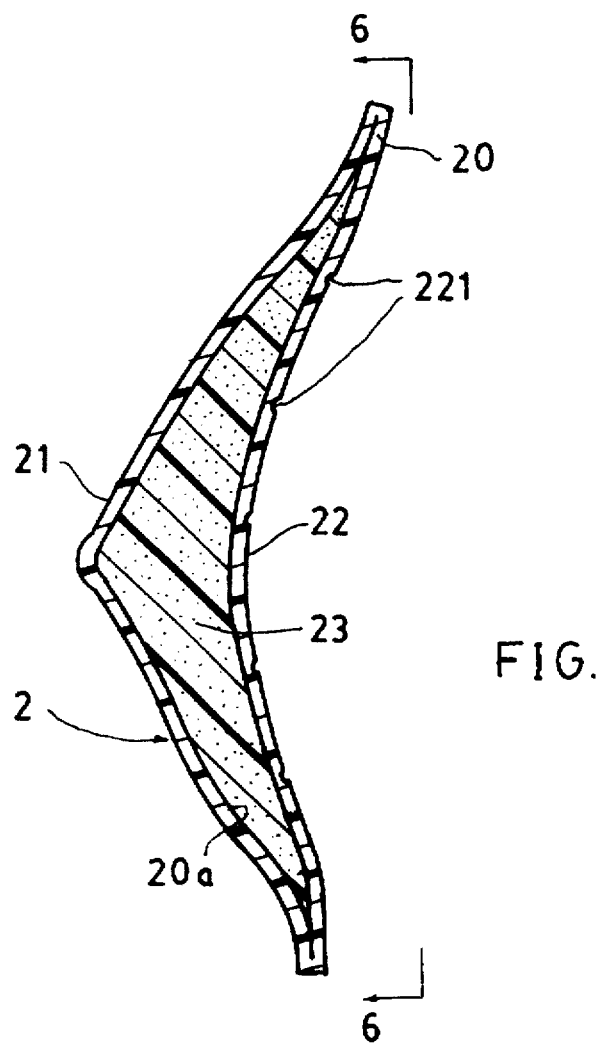
FIG. 5 is a longitudinal sectional drawing of the prosthesis sac of the present invention.
Figure 6:
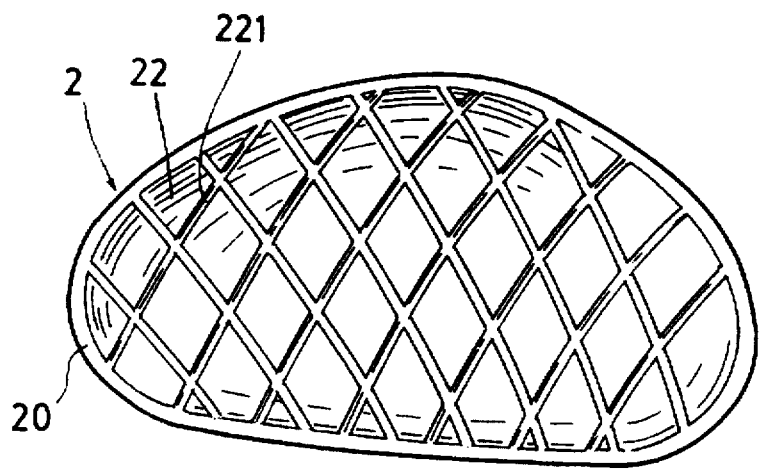
FIG. 6 is a rear view of the sac when viewed from 6—6 direction of FIG. 5.

As shown in FIG. 5, 6, the inner layer 22 of the prosthesis sac 2 is formed with a plurality of grooves 221 recessed in the surface of the inner layer 22 for ventilation and for comfortable wearing of the brassiere when embedding the sac in the brassiere 1.

When inflating the sac 2, the bulb 31 is pumped to boost air into the sac 2 through the adapter 33 of the inflating means 3 and the check valve 25 of the sac 2. The air volume or pressure in the sac interior 20a is optically adjustable by the wearer or user. The air filled into the sac 2 will be homogeneously distributed in the foam core member 23 as formed in the sac 2 to expand the sac 2 mildly and uniformly to have a tender elasticity of the sac 2 to vividly imitate a true female breast and to provide a comfortable wearing of the brassiere when inserting the sac 2 into the pocket 10 of the brassiere 1.

For adjusting the internal air pressure in the sac or for maintenance of the brassiere, the sac 2 may be removed from the brassiere. The inflating means 3 is directly connected with the sac 2 like a part of the sac 2, thereby forming a compact sac having a smooth appearance for a convenient insertion in the brassiere without influencing the wearing of the brassiere on a wearer's body. No tube is provided to connect the bulb 31 and the sac 2 to prevent wearing tangling or obstruction as caused by a conventional brassiere provided with a tube connected between an air pump and the inflatable cup portion of the brassiere.

Figure 7:
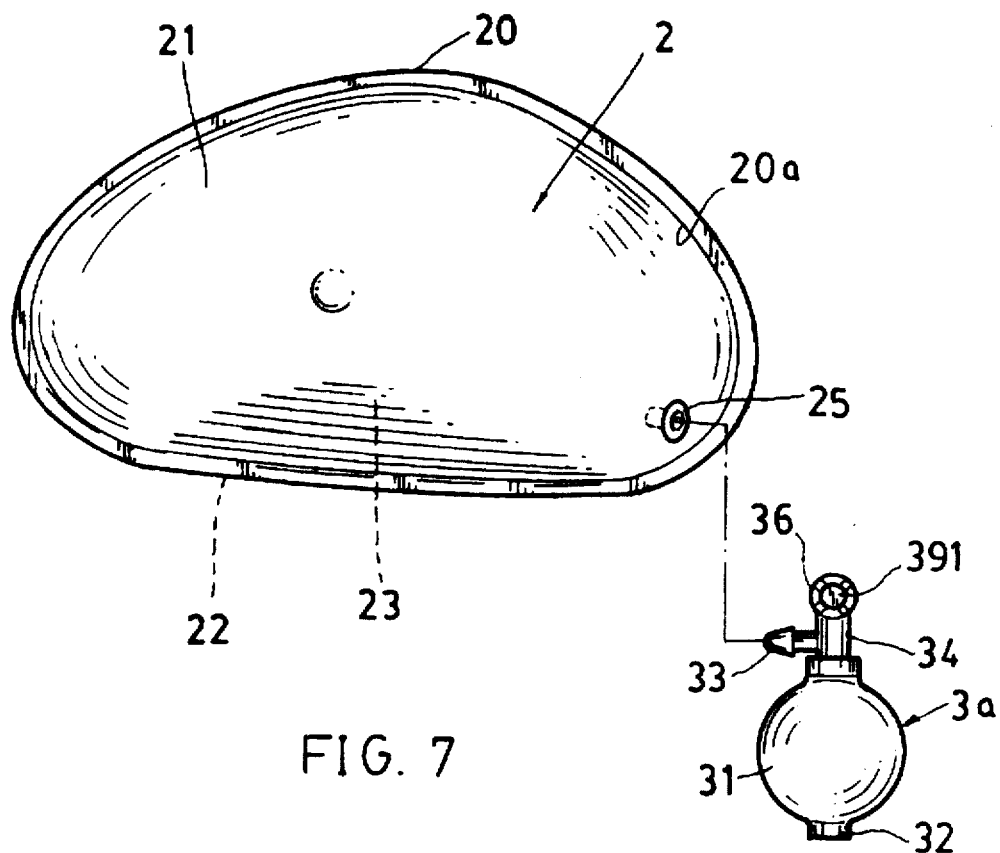
FIG. 7 shows another preferred embodiment of the prosthesis sac in accordance with the present invention.
Figure 8:
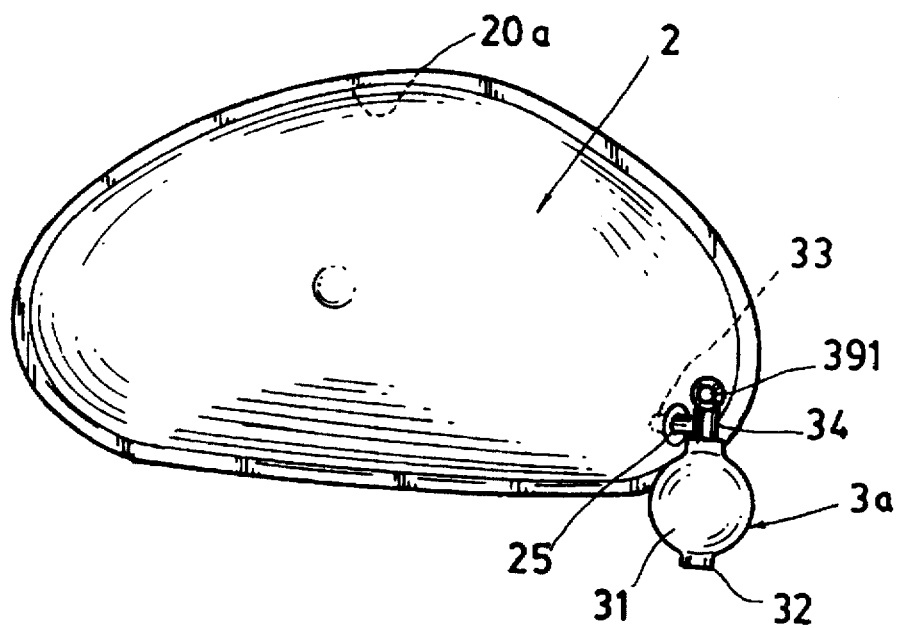
FIG. 8 shows a connection of the prosthesis sac with an inflating and deflating means as shown in FIG. 7.
Figure 9:
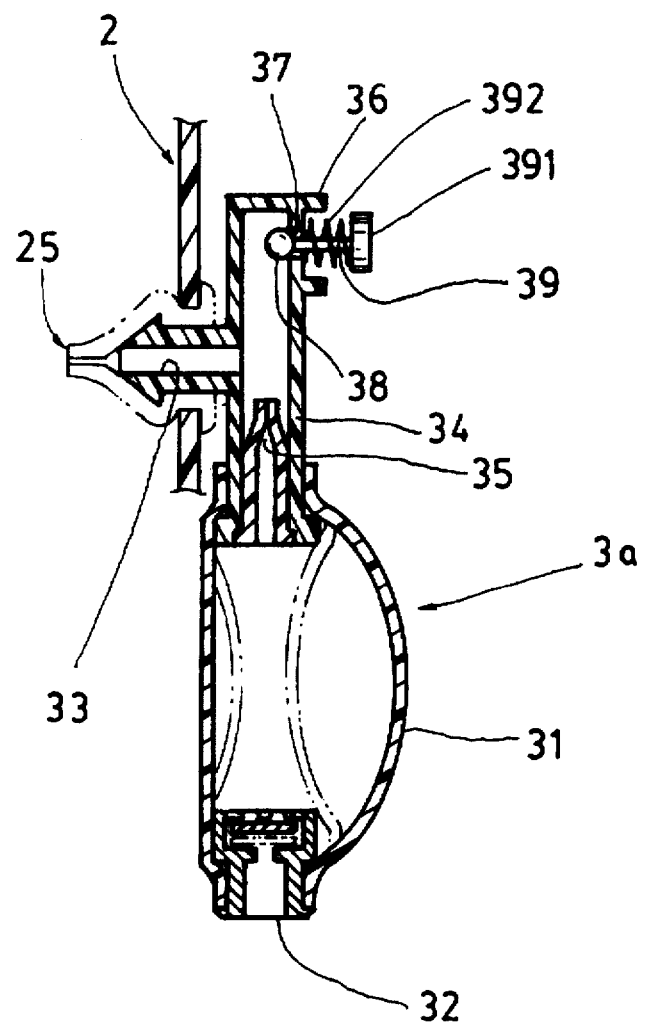
FIG. 9 shows a sectional drawing of the inflating and deflating means of FIG. 7.

Another preferred embodiment of the prosthesis sac 2 is shown in FIGS. 7-9, which includes: an outer layer 21 combinable with an inner layer 22 to define a sac interior 20a between the outer layer 21, the inner layer 22 and a peripheral edge portion 20a by binding an edge portion of each layer, a foam core member 23 filled in the interior 20a, and a prosthesis check valve 25 formed in the sac 2 for connecting an inflating and deflating means 3a in the sac 2 for inflating or deflating the sac 2.

Figure 9A:
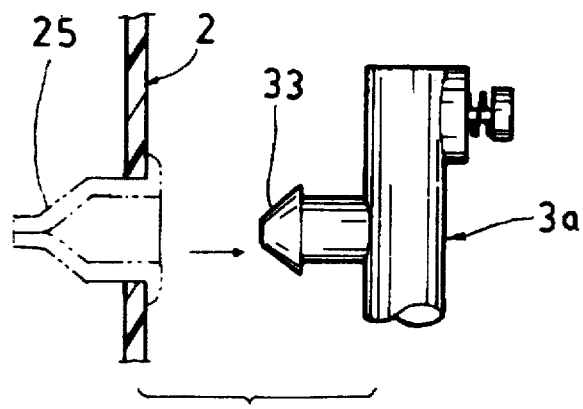
FIG. 9A shows an automatically closed check valve of the sac when removing the inflating and deflating means.

The inflating and deflating means 3a may be separated from the sac 2 as shown in FIG. 7 after finishing the inflation or deflation operation as shown in FIG. 8 when connecting the means 3a on the sac 2. The check valve 25 will be automatically closed when removing the means 3a (FIG. 9A).

The inflating and deflating means 3a as shown in FIG. 9 includes: an inflating bulb 31 having a suction check valve 32 formed on an suction end of the bulb 31 for sucking air into the bulb 31, an adapter 33 connectable with the check valve 25 of the sac 2 and secured to and communicated with a fluid tube 34 connected to an inflating check valve 35 formed on an outlet end of the bulb 31 for inflating the sac 2 when connecting the adapter 33 with the check valve 25 of the prosthesis sac 2, a deflating valve body 36 generally cylindrical shaped and formed on an end portion of the fluid tube 34, a valve opening 37 formed in the valve body 36 for venting air outwardly when the valve opening 37 is opened, a sealing plug 38 connected with a valve stem 39 protruding outwardly beyond the valve opening 37, a push button 391 formed on an outermost end of the valve stem 39 for depressing the push button 391 for lowering the stem 39 and the sealing plug 38 for opening the valve opening 37 when deflating the sac 2, and a restoring spring 392 disposed around the valve stem 39 for urging the push button 391 upwardly for ready for a depression of the push button 391 when deflating the sac 2 and for raising the sealing plug 38 for normally sealing the valve opening 37 when not deflating the sac 2.

After inflation of the sac 2 by the inflating and deflating means 3a, the sac 2 may be inserted into the brassiere 2 and the inflating and deflating means 3a may then be separated from the brassiere which may be stored in a handbag or other suitable locations, thereby further decreasing the weight of the brassiere and enhancing a convenient wearing of the brassiere.

The present invention may be modified without departing from the spirit and scope of the present invention.

I claim:

1. An inflatable prosthesis for insertion in a pocket of a cup portion of a brassiere comprising: an inflatable sac including: an outer layer and an inner layer; said outer and inner layers made of elastic materials and each having an edge portion wherein said layers are attached and bound to each other along said edge portion forming a circumferential peripheral edge portion; said outer layer, said inner layer and said peripheral edge portion defining a sac interior, said sac interior filled with an elastomer form core; said prosthesis further comprising a base extension protruding sidewardly from a side portion of the peripheral edge portion of the inflatable sac, and operatively coupled to a check valve, said check valve for inflating said sac formed in the outer layer of the sac adjacent to the side portion, an inflating means secured to said base extension for inflating said sac; and a venting hole formed in the outer layer of said sac, said venting hole further including a deflating means located therein for deflating the sac.

2. The prosthesis according to claim 1, wherein said inflating means includes an inflating bulb secured on the base extension, said inflating bulb and said base extension circumferentially forming an oval shape, a suction inlet valve formed on an outer end portion of the bulb for sucking air into the bulb, and an adapter formed on an inner portion of the bulb and connectable to said check valve for filling air into the inflatable sac through the adapter and said check valve.

3. The prosthesis according to claim 1, wherein said deflating means includes: a deflating valve body generally cylindrical shaped and inserted in the venting hole in the sac, a valve opening formed in the deflating valve body for venting air outwardly when the deflating means is deflated, a sealing plug connected with a valve stem and protruding outwardly beyond the valve opening, a push button formed on an outermost end of the valve stem for depressing the valve stem and the sealing plug for opening the valve opening for deflating the sac, and a restoring spring disposed about the valve stem urging the push button outwardly to raise the sealing plug for sealing the valve opening, whereby upon depression of the push button, the valve opening is opened to deflate the air in the sac.

4. An inflatable prosthesis for insertion in a pocket of a cup portion of a brassiere comprising: an inflatable sac including an outer layer and an inner layer; each said layer having an edge portion wherein said layers are attached and bound to each other along said edge portion forming a circumferential peripheral edge portion; said outer layer, said inner layer and said peripheral edge portion defining a sac interior, said sac interior filled with a foam core member, and a check valve formed in the sac for connecting an inflating and deflating means to the sac for inflating and deflating the sac; and said inflating and deflating means including: an inflating bulb having a suction check valve formed on a suction end of the bulb for sucking air into the bulb, an inflating check valve formed on an outlet end of the bulb, a fluid tube connectable to the inflating check valve of said bulb, an adapter connectable with the check valve of the sac and secured to said fluid tube for inflating the sac when connecting the adapter with the check valve of the sac, a deflating valve body generally cylindrically shaped and formed on an end portion of the fluid tube, a valve opening formed in the valve body for venting air outwardly when the valve opening is opened, a sealing plug connected with a valve stem and protruding outwardly beyond the valve opening, a push button formed on an outermost end of the valve stem and depressible for lowering the valve stem and the sealing plug for opening the valve opening when deflating the sac, and a restoring spring disposed around the valve stem for urging the push button upwardly, whereby upon a depression of the push button, the valve opening is opened for deflating the sac; and upon raising of the sealing plug, the valve opening is sealed.

5. The inflatable prosthesis according to claim 4, wherein said foam core member is made of polyurethane foam.

* * * * *